(12) United States Patent
Levorse, Jr. et al.

(10) Patent No.: US 7,563,925 B1
(45) Date of Patent: *Jul. 21, 2009

(54) OPTICALLY ACTIVE ESTER COMPOUNDS AND THEIR USE IN PERFUME COMPOSITIONS

(75) Inventors: Anthony T. Levorse, Jr., Westfield, NJ (US); Catherine Marie Smith, Grafton, WI (US); Richard A. Weiss, Livingston, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/120,464

(22) Filed: May 14, 2008

(51) Int. Cl.
C07C 69/34 (2006.01)
A61K 8/18 (2006.01)

(52) U.S. Cl. ......................... 560/193; 512/22

(58) Field of Classification Search ................ None
See application file for complete search history.

(56) References Cited

U.S. PATENT DOCUMENTS 6,774,260 B2 * 8/2004 Bledsoe et al. ............... 560/193
6,919,477 B2 * 7/2005 Bledsoe et al. ............... 560/193

OTHER PUBLICATIONS

Ansari, H.R. "Cyclisation of optically active dihydromyrcenes (2,6-dimethyl-2,7-octadiene): A stereospecific ring contraction." Tetrahedron (1973) 29(11), pp. 1559-1564.

Wu, J. et al. "Air-Stable Catalysts for Highly Efficient and Enantioselective Hydrogenation of Aromatic Ketones." J. Org. Chem. (2002) 67(22), pp. 7908-7910.

Kraft, P. et al. "Synthesis and Odor of Aliphatic Musks: Discovery of a New Class of Odorants." Eur. J. Org. Chem. (2004) 2, pp. 354-365.

* cited by examiner

*Primary Examiner*—Karl J Puttlitz
(74) *Attorney, Agent, or Firm*—Elizabeth M. Quirk; XuFan Tseng; Joseph F. Leightner

(57) ABSTRACT

Optically active ester compounds of the formula:

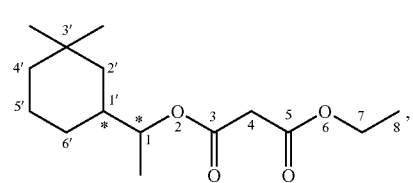

Formula I in particular,

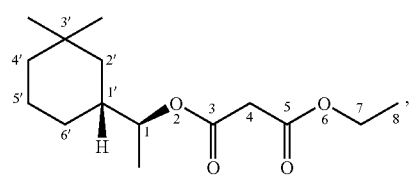

Formula III are useful fragrance materials.

13 Claims, No Drawings

OPTICALLY ACTIVE ESTER COMPOUNDS AND THEIR USE IN PERFUME COMPOSITIONS

FIELD OF THE INVENTION

The present invention relates to optically active ester compounds and the incorporation and use thereof as fragrance materials.

BACKGROUND OF THE INVENTION

Molecular chirality study has become one of the most important frontiers in exploratory organic synthetic research. The activities of many pharmaceuticals, fragrances, food additives, and agrochemicals are often associated with their chiral configuration. A compound of a wrong enantiomeric form may lack desirable biological, physical or chemical properties. In the fragrance industry, there is an ongoing need to provide new chemicals including new chiral compounds to give perfumers and other persons the ability to create new fragrances for perfumes, colognes and personal care products. However, identifying a chiral center and developing a cost-effective process to synthesize enantiomers and/or targeted racemic compounds pose difficult challenges, let alone discovering an active form is unpredictable as such effort may often not lead to a desirable enantiomer that exhibits a stronger fragrance effect than the others and/or its racemic mixture.

The present invention concerns novel optically active ester compounds represented by Formulas I set forth below:

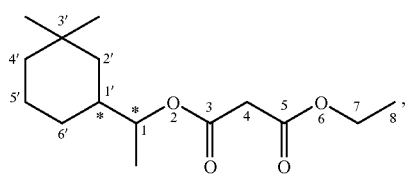

Formula I wherein * indicates a chiral center.

The racemic compounds of Formula I are known in the art. U.S. Pat. Nos. 6,774,260 and 6,919,477, both belonging to the present Applicants, disclose the compound ethyl 1-(3,3-dimethyl-1'-cyclohexyl)ethyl malonate with absolute configuration of "R" or "S" at carbon 1 position. However, the additional chiral center at carbon 1' position has never been taught or suggested in the art. The present invention discloses in particular an enantiomer involving the newly identified chiral center and its related racemic compounds as well as their unexpected advantageous use in perfumery.

SUMMARY OF THE INVENTION

The present invention provides optically active ester compounds, and the use of these compounds to enhance the fragrance of perfumes, toilet waters, colognes, personal products and the like.

Specifically, the present invention discloses the fragrance compounds and a method of improving, enhancing or modifying a fragrance formulation through the addition of an olfactory acceptable amount of compounds represented by Formulas I set forth below:

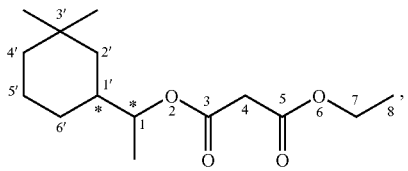

Formula I wherein * indicates a chiral center. In particular, the following compounds are disclosed:

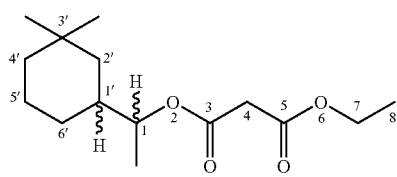

Formula II

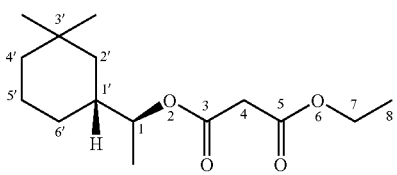

Formula III

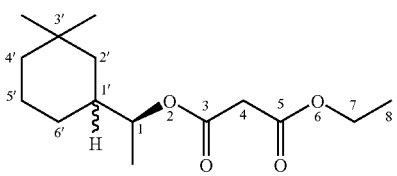

Formula IV

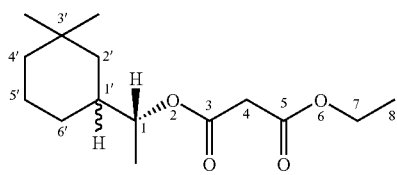

Formula V

The present invention is directed to the surprising finding of the chiral center at carbon 1' position in the above compounds, which has never been taught or suggested in the art.

The present invention is also directed to a method for enhancing a perfume composition by incorporating an olfactory acceptable amount of the optically active ester compounds as defined above.

These and other embodiments of the present invention will be apparent by reading the following specification.

DETAILED DESCRIPTION OF THE INVENTION

It has been surprisingly discovered that the ester compounds of the present invention as defined above contain a chiral center at carbon 1' position, which was not known in the art. Thus, the existence of enantiomers involving this chiral center would have been considered unlikely, let alone the making of stable enantiomers and their targeted racemic mixtures. In addition, the optically active enantiomeric form of the present invention is unexpectedly found to be distinctly advantageous, as regards perfumery applications, when compared to the previously known racemic mixture counterparts.

Specifically, the present invention discloses the optically active ester compounds of the following:

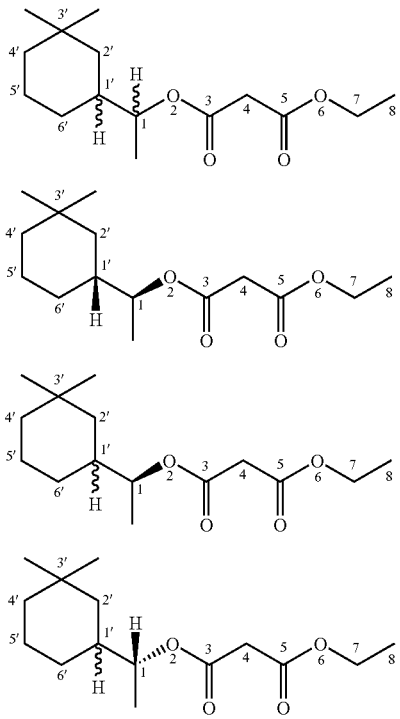

Formula II

Formula III

Formula IV

Formula V

Those with the skill in the art will appreciate that:

Formula II is (+/−)-(1RS,1'RS)-1-(3',3'-dimethyl-1'-cyclohexyl)ethyl ethyl malonate;

Formula III is (+)-(1S,1'R)-1-(3',3'-dimethyl-1'-cyclohexyl)ethyl ethyl malonate;

Formula IV is (+)-(1S,1'RS)-1-(3',3'-dimethyl-1'-cyclohexyl)ethyl ethyl malonate; and Formula V is (−)-(1R,1'RS)-1-(3',3'-dimethyl-1'-cyclohexyl)ethyl ethyl malonate.

In one embodiment of the invention, the compounds represented by Formula II, Formula III, and Formula IV are preferred compounds.

In another embodiment of the invention, a compound represented by Formula III (i.e., (+)-(1S,1'R)-1-(3',3'-dimethyl-1'-cyclohexyl)ethyl ethyl malonate) is a preferred compound.

The compounds of the present invention may be prepared from chiral alcohol and diethyl malonate as exemplified by a general scheme depicted as follows:

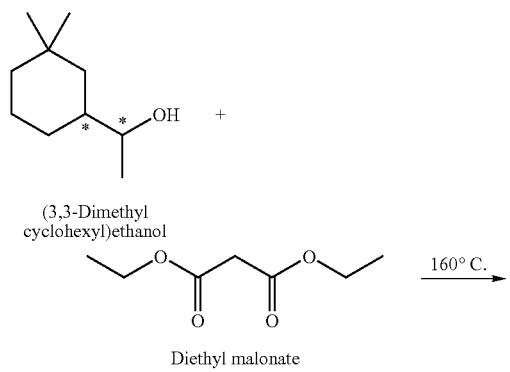

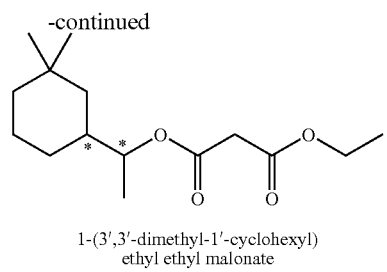

1-(3',3'-dimethyl-1'-cyclohexyl)ethyl ethyl malonate

The starting chiral alcohols are either commercially available or can be made by methods detailed in the below examples of the present invention.

We have discovered that the compounds of the present invention have fruity and musky characters that are well suited for use as a fragrance ingredient. In particular, Formula III possesses a complex odor character of powerful musky, fruity, woody, and ambery notes.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in Perfumes Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compounds of the invention employed in a perfumed article varies from about 0.005 to about 10 weight percent, preferably from about 0.5 to about 8 and most preferably from about 1 to about 7 weight percent. Further, it is preferred to employ the compound represented by Formula III with an optical purity of about 60% enantiomeric excess (ee) or greater, more preferred of about 80% ee or greater, still more preferred of about 90% ee or greater, and even more preferred of about 98% ee or greater. In addition to the compounds of the invention, other agents can be used in conjunction with the perfumed article. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

When used in a fragrance formulation this ingredient provides freshness making the fragrance top notes more desirable and noticeable. It also has a spicy peppery odor which is very commonly used in men's fragrances added for fragrance appropriateness and desirability. The woody part of it is very useful in both men's and women's fragrances adding body and substantivity to the finished product. All of these odor qualities found in this material assist in beautifying and enhancing the finished accord improving the performance of the other materials in the fragrance. The floral of it will beautify as well and makes the fragrance more desirable and add the perception of value. There is also the fruity side of it which is found in many fragrances today which happens to be very trendy, especially for the younger consumer.

The following are provided as specific embodiments of the present invention. Other modifications of this invention will be readily apparent to those skilled in the art. Such modifications are understood to be within the scope of this invention. As used herein all percentages are weight percent unless otherwise noted, and g is understood to be gram. IFF as used in the examples is understood to mean International Flavors & Fragrances Inc., New York, N.Y., USA.

EXAMPLE I

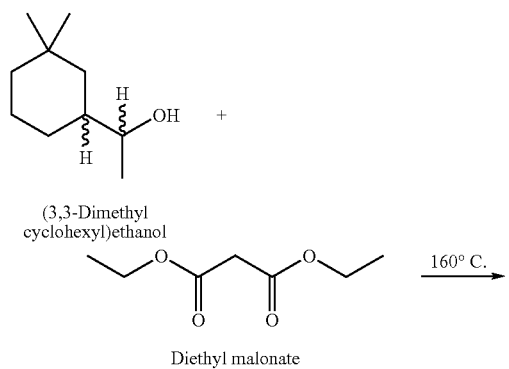

(3,3-Dimethyl cyclohexyl)ethanol

Diethyl malonate

160° C.

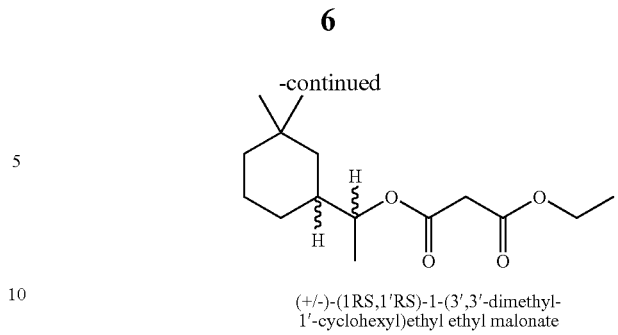

(+/−)-(1RS,1'RS)-1-(3',3'-dimethyl-1'-cyclohexyl)ethyl ethyl malonate

Preparation of (+/−)-(1RS,1'RS)-1-(3',3'-dimethyl-1'-cyclohexyl)ethyl ethyl malonate: (+/−)-(1RS,1'RS)-1-(3',3'-dimethyl-1'-cyclohexyl)ethyl ethyl malonate (Formula II) was prepared according to the above process disclosed in U.S. Pat. No. 6,774,260. A solution of 250 g of (3,3-dimethylcyclohexyl)ethanol (CP-Alcohol, IFF) and 1000 g of diethyl malonate (commercially available from Aldrich Chemical Company, Inc., Milwaukee, Wis.) was heated to 160° C., while distilling off ethanol. Vacuum distillation provided 405 g of product (Formula II).

The boiling point of the product was 138° C. at 3.5 millimeters of mercury.

The NMR analysis of the product is the following: 0.81-1.66 ppm (m, 9H); 0.88 ppm (s, 3H); 0.91 ppm (s, 3H); 1.19 ppm (d, 3H, J=6.4 Hz); 1.29 ppm (t, 3H, J=7.1 Hz); 3.35 ppm (s, 4H); 4.21 ppm (q, 2H); 4.75 ppm (m, 1H).

The compound was described as having fruity, apple, and musky notes.

EXAMPLE II

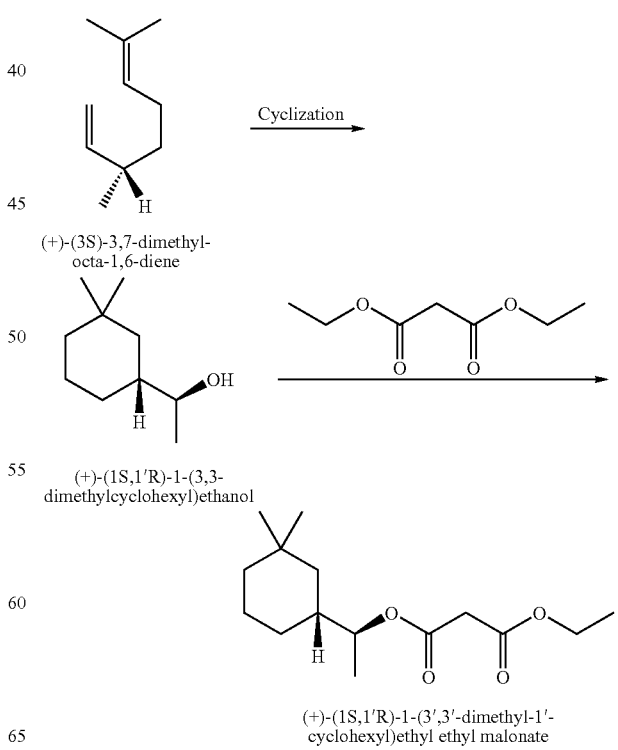

(+)-(3S)-3,7-dimethyl-octa-1,6-diene

Cyclization (+)-(1S,1'R)-1-(3,3-dimethylcyclohexyl)ethanol (+)-(1S,1'R)-1-(3',3'-dimethyl-1'-cyclohexyl)ethyl ethyl malonate Preparation of (+)-(1S,1'R)-1-(3',3'-dimethyl-1'-cyclohexyl) ethyl ethyl malonate: First, chiral alcohol (+)-(1S,1'R)-1-(3', 3'-dimethylcyclohexyl)ethanol was obtained from (+)-(3 S)-3,7-dimethyl-octa-1,6-diene (commercially available from IFF) according to the process described by Ansari, H. R. (Tetrahedron (1973) 29, 1559-1564). The resulting chiral alcohol and diethyl malonate were reacted according to the process detailed in Example I to provide (+)-(1S,1'R)-1-(3', 3'-dimethyl-1'-cyclohexyl)ethyl ethyl malonate (Formula III) with an optical rotation of $[\alpha]_D^{25}=+4.6$ (c=1).

Chiral GC analysis showed the enantiomeric excess for the product was 95% ee.

The compound was described as having powerful musky, fruity, woody, and ambery notes.

EXAMPLE III

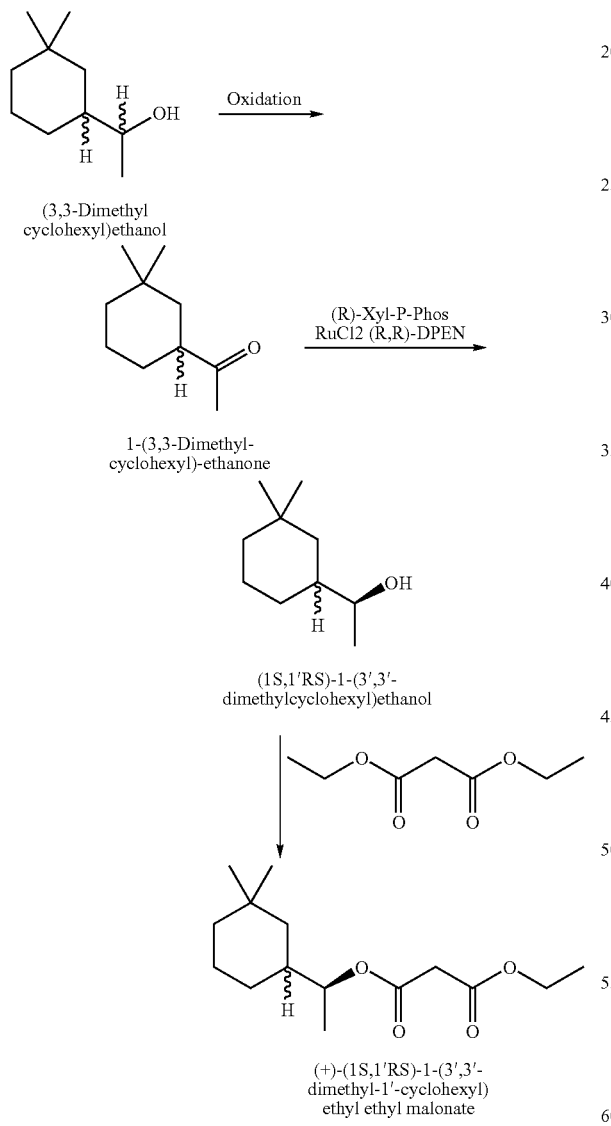

Preparation of (+)-(1S,1'RS)-1-(3',3'-dimethyl-1'-cyclohexyl)ethyl ethyl malonate: (3,3-dimethylcyclohexyl)ethanol was oxidized to provide 1-(3,3-dimethyl-cyclohexyl)-ethanone (Herbac®, IFF), which was subsequently reduced using asymmetric hydrogenation catalyst (R)-Xyl-P-Phos RuCl2 (R,R)-DPEN as described by Chen et at. (J. Org. Chem. (2002) 67, 7908-7910) to provide (1S,1'RS)-1-(3',3'-dimethylcyclohexyl)ethanol. The resulting chiral ethanol was further reacted with diethyl malonate according to the process detailed in Example I to provide (+)-(1S,1'RS)-1-(3',3'-dimethyl-1'-cyclohexyl)ethyl ethyl malonate (Formula IV) with an optical rotation of $[\alpha]_D^{25}=+0.16$ (c=1).

The compound was described as having musky, fruity, honey, woody, and ambery notes.

EXAMPLE IV

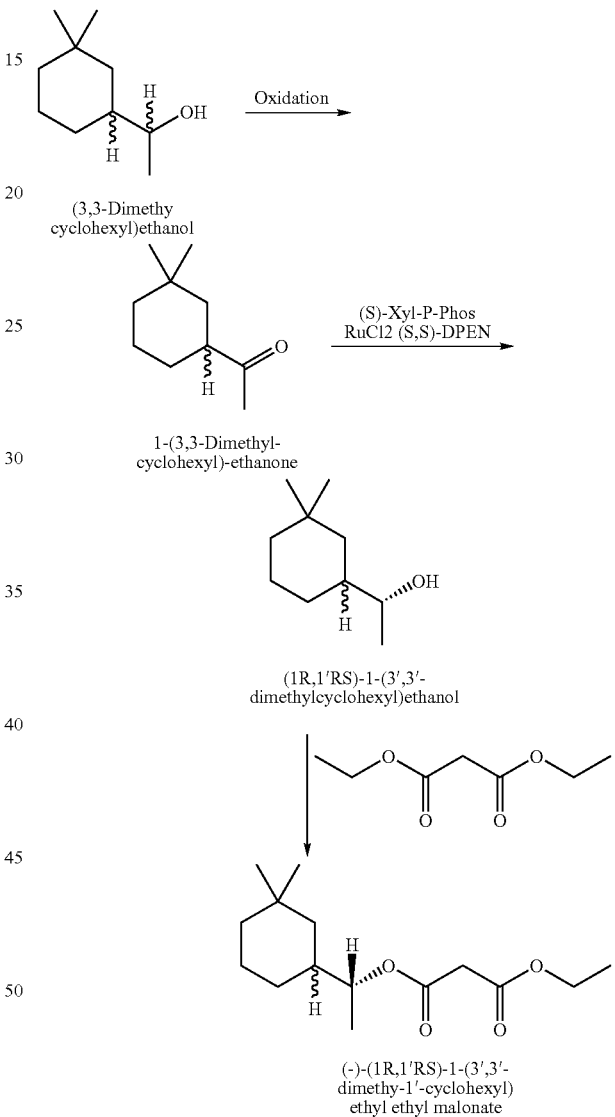

Preparation of (−)-(1R,1'RS)-1-(3',3'-dimethyl-1'-cyclohexyl)ethyl ethyl malonate: As described in Example III, 1-(3,3-dimethyl-cyclohexyl)-ethanone was obtained, which was subsequently reduced using asymmetric hydrogenation catalyst (S)-Xyl-P-Phos RuCl2 (S,S)-DPEN according to Wu et al. (J. Org. Chem. (2002) 67, 7908-7910) to produce (1R, 1'RS)-1-(3',3'-dimethylcyclohexyl)ethanol. The resulting chiral ethanol was then reacted with diethyl malonate according to the process detailed in Example I to provide (−)-(1R, 1'RS)-1-(3',3'-dimethyl-1'-cyclohexyl)ethyl ethyl malonate (Formula V) with an optical rotation of $[\alpha]_D^{25}=-0.21$ (c=1).

The compound was described as having musky, honey, fruity, and woody notes.

EXAMPLE V

The odors and odor intensity for compounds of Formulas II, III, IV, and V were identified and evaluated on a 0-10 odor intensity scale, 0 being no odor detected, 10 being extremely strong odor present.

| Compound | Odor intensity (1-10) | Odor descriptor |
| --- | --- | --- |
| Formula II | 5.0 | Fruity, Apple, Musky |
| Formula III | 7.5 | Powerful Musky, Fruity, Woody, Ambery |
| Formula IV | 6.0 | Musky, Fruity, Honey, Woody, Ambery |
| Formula V | 4.0 | Masky, Dirty Honey, Fruity, Woody |

The above odor profile demonstrates Formula III possesses surprisingly strong odor characters of powerful musky, fruity, woody, and ambery.

EXAMPLE VI

The odors of Formulas II and III were further evaluated and demonstrated in the following fragrance compositions:

| Ingredients | Parts by Weight | Parts by Weight |
| --- | --- | --- |
| Ethyl Vanillin 10% DGP | 5.00 | 5.00 |
| Khrasimal | 10 | 10 |
| Vanillin ex Lignin 10% DPG | 10 | 10 |
| Ambrette Seed Oil | 0.30 | 0.3 |
| Patchouli Oil 10% DPG | 5.0 | 5.0 |
| Amberiff crystals 1% DPG | 10 | 10 |
| Bergamot Essential Oil | 40 | 40 |
| DPG | 131.7 | 295.2 |
| (+/−)-(1RS, 1'RS)-1-(3',3'-dimethyl-1'-cyclohexyl) ethyl ethyl malonate (Formula II) | 218 | — |
| (+)-(1S, 1'R)-1-(3',3'-dimethyl-1'-cyclohexyl)ethyl ethyl malonate (Formula III) | — | 54.5 |
| Total weight | 430 | 430 |

The above fragrance composition of Formula II has a clean oriental odor character; and the fragrance composition of Formula III has a more perfumery lift and a more sensual oriental odor character.

What is claimed is:

1. A compound, said compound being (+)-(1S,1'R)-1-(3',3'-dimethyl-1'-cyclohexyl)ethyl ethyl malonate.

2. A composition comprising the compound of claim 1 having an enantiomeric excess of about 60% ee or greater.

3. A composition comprising the compound of claim 1 having an enantiomeric excess of about 80% ee or greater.

4. A composition comprising the compound of claim 1 having an enantiomeric excess of about 90% ee or greater.

5. A composition comprising the compound of claim 1 having an enantiomeric excess of about 98% ee or greater.

6. A method of improving, enhancing or modifying a fragrance formulation through the addition of an olfactory acceptable amount of a compound, said compound being (+)-(1S,1'R)-1-(3',3'-dimethyl-1'-cyclohexyl)ethyl ethyl malonate.

7. The method of claim 6, wherein the fragrance formulation is incorporated into a product selected from the group consisting of a perfume, a cologne, a toilet water, a cosmetic product, a personal care product, a fabric care product, a cleaning product, and an air freshener.

8. The method of claim 7, wherein the cleaning product is selected from the group consisting of a detergent, a dishwashing composition, a scrubbing compound, and a window cleaner.

9. The method of claim 6, wherein the olfactory acceptable amount is from about 0.005 to about 10 weight percent of the fragrance formulation.

10. The method of claim 6, wherein the olfactory acceptable amount is from about 0.5 to about 8 weight percent of the fragrance formulation.

11. The method of claim 6, wherein the olfactory acceptable amount is from about 1 to about 7 weight percent of the fragrance formulation.

12. A fragrance formulation containing an olfactory effective amount of the compound of claim 1.

13. A fragrance product containing an olfactory effective amount of the compound of claim 1.

* * * * *